United States Patent [19]
Stivison et al.

[11] Patent Number: 5,388,707
[45] Date of Patent: Feb. 14, 1995

[54] APPARATUS FOR INSPECTING THE EXTERIOR FINISH OF CONTAINERS AND ASSOCIATED METHOD

[75] Inventors: Lloyd Stivison, West Sunbury; Henry Dimmick, Sr., Butler, both of Pa.

[73] Assignee: AGR International, Inc., Butler, Pa.

[21] Appl. No.: 906,589

[22] Filed: Jun. 30, 1992

[51] Int. Cl.⁶ ............................ B07C 5/07; B07C 5/12
[52] U.S. Cl. ............................ 209/602; 209/533; 209/701; 209/934; 198/389; 198/415; 33/522; 33/783
[58] Field of Search ............... 209/522, 523, 529, 530, 209/531, 533, 538, 934, 600, 601, 602, 701; 33/501.04, 501.06, 522, 545, 555.1, 783; 198/389, 415, 836.2

[56] References Cited

U.S. PATENT DOCUMENTS

| | | | |
|---|---|---|---|
| 2,988,218 | 6/1961 | Fedorchak et al. | 209/525 X |
| 3,706,369 | 12/1972 | Ishida et al. | 198/389 |
| 3,782,542 | 1/1974 | Scribner | 209/530 X |
| 3,823,815 | 7/1974 | Bretten et al. | 198/415 X |
| 3,923,158 | 12/1975 | Fornaa | 209/531 X |
| 4,239,570 | 12/1980 | Kerwin | 198/415 X |
| 5,088,207 | 2/1992 | Betsill et al. | 33/783 X |

*Primary Examiner*—D. Glenn Dayoan
*Assistant Examiner*—Tuan N. Nguyen
*Attorney, Agent, or Firm*—Arnold B. Silverman; George K. Stacey

[57] ABSTRACT

Apparatus and method are provided for inspecting finish dimensions of and detecting finish defects on containers moving sequentially in a predetermined path. More than one container can be inspected simultaneously. The apparatus includes one or more inspection gauges suspended above the container path. A transport system is provided for aiding in moving containers through the gauges and simultaneously axially rotating the containers about a vertical axis. Rotation of the containers allows the inspection gauges to inspect the entire circumference of the containers at one or more levels on the container simultaneously. Defective containers are detected when the relative separation distance between the gauge plates of the inspection gauge falls outside predetermined limits. If a defective container is detected, a rejection assembly may be activated to physically remove the defective container from the container path. A suspension system permits transverse movement of the inspection gauges to accommodate non-concentric containers therethrough. The method of this invention includes inspecting containers using in the apparatus of this invention.

18 Claims, 6 Drawing Sheets

APPARATUS FOR INSPECTING THE EXTERIOR FINISH OF CONTAINERS AND ASSOCIATED METHOD

BACKGROUND OF THE INVENTION

1. Field of the Invention

This invention relates to the inspection of containers and, more particularly, to apparatus and methods for inspecting such containers for finish dimensions and finish defects or irregularities.

2. Brief Description of the Prior Art

Inspecting containers to ensure that finish dimensions fall within acceptable tolerances and to detect surface defects is important in modern container manufacturing, processing and filling operations. For example, finish defects and containers of improper size can damage on-line production machines, cause of loss of product and result in unusable, or even dangerous, containers.

Some finish defects that typically occur in blown plastic bottles include blown finish defects, skirt defects, and improper dimensions. Blown finish defects often occur when the finish of the container overhears in the blow molding process and the container finish splits or otherwise deforms during the application of pressure to expand the container preform into the mold. Skirt defects may include non-parallel sides of the safety ring groove that result in such groove being of incorrect depth. Improper dimensions can result in non-capable containers and/or can permit removal of the safety or locking ring of the closure from the container without removal of the cap.

Containers may be manually inspected for finish defects and proper finish dimensions. Manual inspection has several disadvantages. It is extremely difficult to detect or remove containers with oversized dimensions from container production lines using manual inspection. In addition, modern production lines, such as container manufacturing and filling operations, typically operate at very high speeds. For example, such lines may operate at speeds on the order of 25,000 containers per hour or higher. Manual inspection of containers moving at such speeds is difficult.

Many types of automated apparatus for inspecting containers are known. For example, U.S. Pat. Nos. 2,937,749; 2,988,218; 3,782,542; 3,249,223; and 3,815,248 disclose apparatus for inspecting various exterior dimensions of containers.

In addition, U.S. Pat. Nos. 3,273,710 and 3,196,550 disclose apparatus for inspecting containers for the presence of surface irregularities and to detect whether the containers are of proper height.

U.S. Pat. No. 4,433,785 discloses an apparatus for determining whether the bottom of the container is perpendicular to the vertical axis of the container. It has also been known to rotate the container being inspected about its vertical axis during inspection thereof. Such rotation enables the entire circumference of the container at the level of inspection to be inspected.

It has also been known to inspect the thickness of containers using multiple sensors so that more than one container can be inspected simultaneously. U.S. Pat. No. 5,097,216 discloses a method and apparatus for inspecting the thickness of more than one container simultaneously using multiple sensors.

Despite the prior art, there remains a need for an apparatus and method for inspecting the finish of containers which provide simple and more reliable measurement of the finish dimensions of and detection of finish defects or irregularities on containers while such containers are moving sequentially at relatively high speeds. In addition, there remains a need for apparatus and method of inspecting containers which can simultaneously inspect more than one container at more than one location or level.

SUMMARY OF THE INVENTION

The present invention has met the above-described needs.

This invention provides an apparatus for inspecting containers moving sequentially in a predetermined path. The apparatus includes at least one inspection gauge positioned above the path of movement of the containers, transport means for aiding and moving the containers through the inspection gauge and for simultaneously axially rotating the containers about a vertical axis. The inspection gauges are spaced apart such that only one container can be in each gauge at a time. The use of more than one inspection gauge enables more than one container to be inspected simultaneously. Each inspection gauge preferably includes a pair of elongated, generally opposed gauge plates mounted for pivotal movement relative to one another at a first pivot point on upper ends thereof, sensor means for detecting defective containers, return spring means for urging the gauge plates into a closed position, and dampening means for reducing rebound movement of the gauge plates upon closure thereof.

The gauge plates have gauging means thereon for engaging containers passing therebetween at at least one pair of generally diametrically opposed locations on the containers. Engagement of the gauge plates and containers allows the exterior finish of the containers to be inspected for proper dimensions and for the presence of surface defects or irregularities. It is preferred that the gauge plates engage each container at more than one such pair of locations so that dimensions can be measured and defects inspected for simultaneously at more than one level on the container. For example, it may be desirable to simultaneously inspect the threads on a neck portion of the container, the skirt portion of the neck of the container, and a flanged portion of the neck of the container adjacent to the threads.

The sensor means is operative responsive to relative movement of the gauge plates. The sensor means detects a defective container when the relative separation distance between the gauge plates where they engage the container falls outside predetermined limits. When a properly sized and non-defective container passes between the gauge plates, the plates remain closed. A defective container causes the gauge plates to separate, thereby activating the sensor means.

The transport means includes means for engaging the containers, sequentially effecting translational movement of the containers through the gauges and simultaneously rotating the containers about a vertical axis. The transport means may also lift the containers that are engaged thereby. Rotation of the container as it passes through the gauges allows substantially the entire circumference of the container at the inspection to be inspected. The total length of the gauge plates is preferably such that substantially the entire circumference of each container being inspected is inspected at each inspection location or level.

A suspension system may be provided to suspend the gauges above the path of the containers. The suspension system may include a suspension bar having one end pivotally connected to the gauge at a second pivot point located at or above the first pivot point. The other end of the suspension bar may be pivotally attached to a frame. The suspension system permits transverse pivotal movement of the gauge so that non-concentric containers may pass therethrough.

The sensor means may be in communication with reject means for identifying defective containers detected by the sensor means. Reject means may include a rejection assembly for physically removing defective containers from the path of the containers after such defective containers have been detected by the sensor means.

Inspection can be stopped and started without disrupting the flow of movement of the containers. Means may be provided for opening and closing the inspection gauge without interfering with the moving containers. In addition, means may be provided for moving the transport means into and out of the inspection position without disrupting the moving containers.

The method of this invention includes moving a container to be inspected through the apparatus of this invention, as described hereinbefore, and rotating the container about its vertical axis to bring substantially the entire circumference of the portion of the container being inspected into contact with the gauge plates of the gauge for inspection of the container. By using more than one inspection gauge, more than one container can be inspected simultaneously. Other containers can be moved into the apparatus before the preceding containers exit the apparatus. For example, if four inspection gauges are provided, up to four containers can be inspected simultaneously.

Each container is inspected about its circumference at the level of at least one pair of generally diametrically opposed locations on the container. Each inspection gauge may be pivotally moved in transverse directions to permit non-concentric containers to pass therethrough.

It is an object of this invention to provide an apparatus and method for inspecting the finish of containers for proper dimensions and for the presence of surface defects or irregularities.

It is another object of this invention to provide an apparatus and method for inspecting containers about substantially the entire circumference of the containers at at least one axial location, or level, thereon.

It is yet another object of this invention to provide an apparatus and method for sequentially inspecting containers traveling at high speeds sequentially in a predetermined path without having to stop the containers or change the general direction of movement of such containers.

It is an object of this invention to provide an apparatus and method for inspecting containers which are particularly useful for inspection of the neck region of containers, including threaded or lugged areas of the neck region.

It is a further object of this invention to provide an apparatus and method for inspecting generally cylindrical containers, such as bottles and jars, of the type which are commonly used in the food and beverage packaging industry.

It is still another object of this invention to provide an apparatus and method for inspecting containers which are particularly useful in inspecting external portions of such containers.

It is a further object of this invention to provide an apparatus and method for inspecting containers which can be used to inspect every container in the container movement path rather than inspecting only representative samples of such containers.

It is another object of this invention to provide an apparatus and method for inspecting containers which can be used to simultaneously inspect such containers at one or more levels on each container.

It is a further object of this invention to provide an apparatus and method for inspecting containers which can be used to simultaneously inspect more than one container.

It is still another object of this invention to provide an apparatus and method for inspecting containers which can be used to inspect concentric and non-concentric containers.

It is a further object of this invention to provide an apparatus and method for inspecting containers which can be used in association with a reject means to identify defective containers detected during inspection and remove such defective containers from the predetermined path of container movement, or production line.

It is yet another object of this invention to provide an apparatus and method for inspecting containers where such containers are made of glass, plastic or similar materials.

It is still another object of this invention to produce an apparatus and method for inspecting containers wherein inspection can be selectively stopped and started without disrupting the movement of the containers.

These and other objects of this invention will be more fully understood from the following description on reference to the illustrations appended hereto.

A BRIEF DESCRIPTION OF THE DRAWINGS

DESCRIPTION OF A PREFERRED EMBODIMENT

Figure 1:
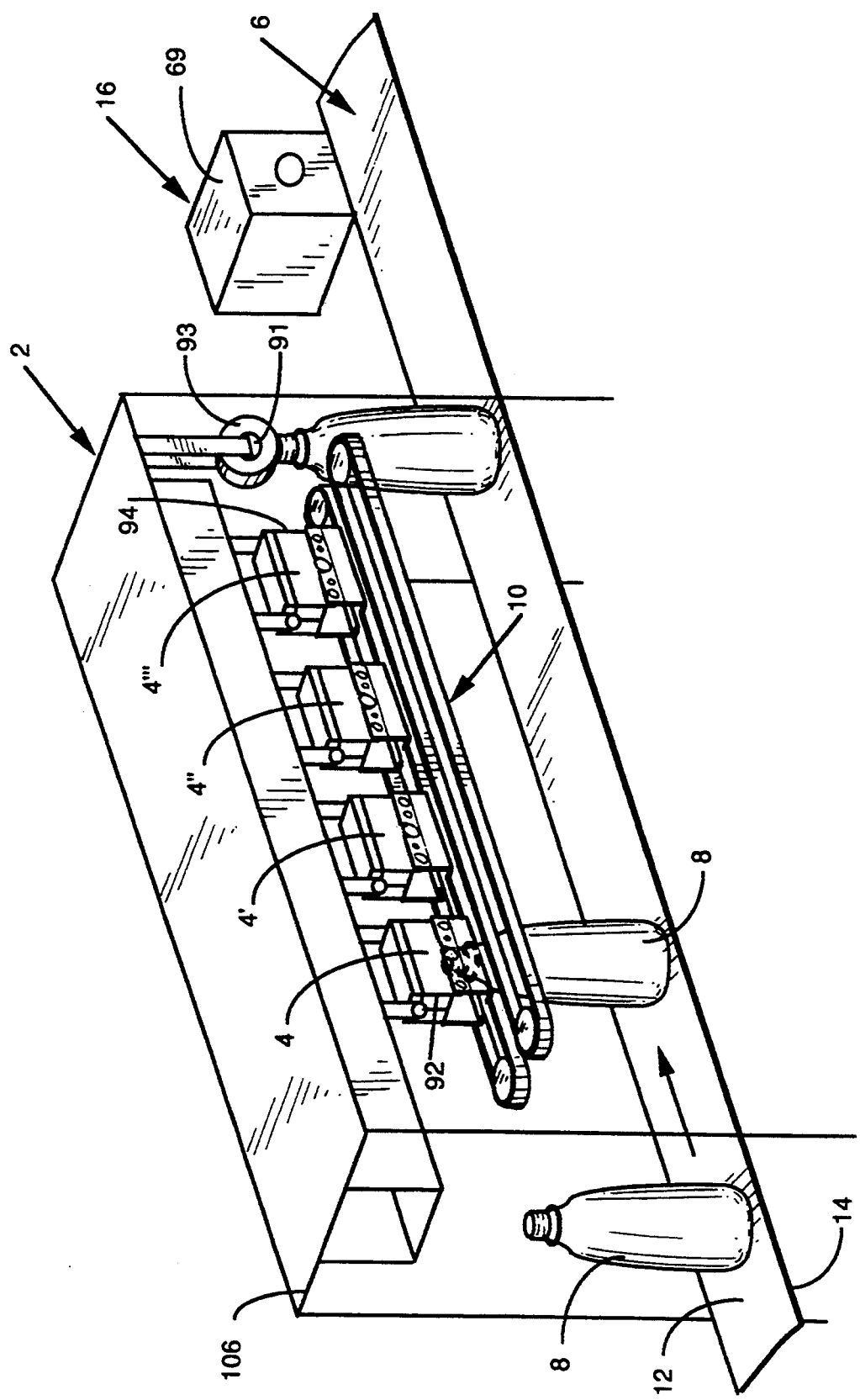
FIG. 1 is a perspective view of an embodiment of the container inspection apparatus of this invention.
Figure 2:
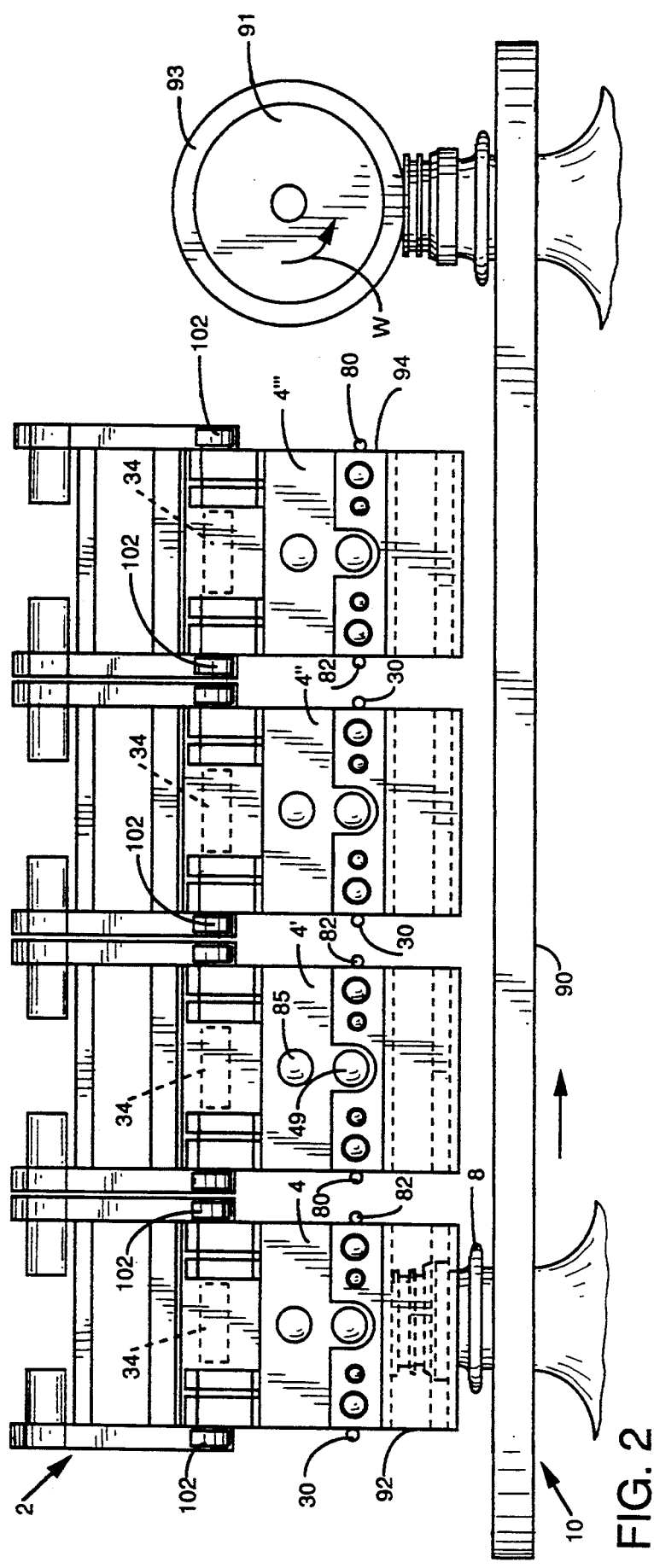
FIG. 2 is a side view of a portion of the apparatus shown in FIG. 1.
Figure 3:
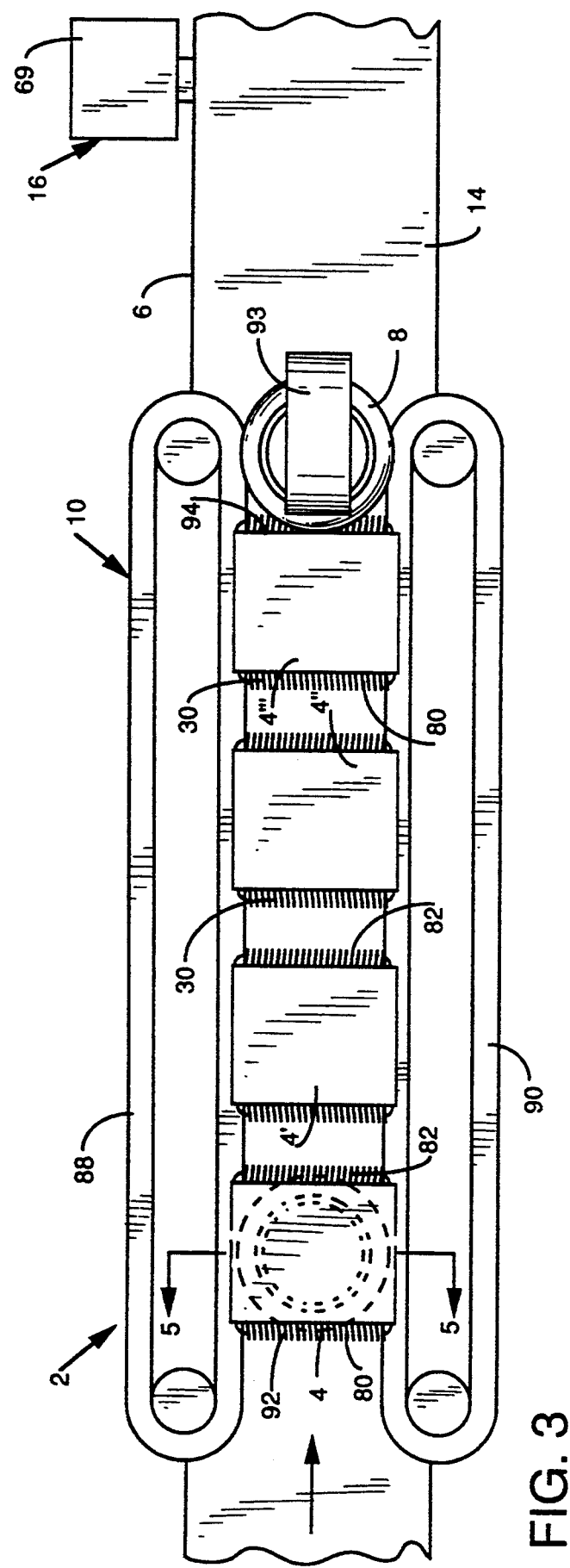
FIG. 3 is a plan view of the apparatus of FIG. 1 with the frame removed.

Referring to FIGS. 1 through 3, the container inspection apparatus 2 of this invention includes at least one inspection gauge 4, 4', 4", 4'" positioned generally above the path 6 of moving containers 8, and transport means 10 for aiding in moving containers 8 sequentially through inspection gauges 4, 4', 4'', 4'''. Containers 8 preferably move in a generally linear predetermined path 6. In a preferred embodiment, predetermined path 6 is defined by a production line 12. Production line 12 may include a conveyor 14 for moving containers sequentially in the predetermined path. Production line 12 may be part of a container handling system as is typically used in container manufacturing. It will be appreciated that containers moving on production line 12 may be emerging from a container forming operation, and will be moved through inspection gauges 4, 4', 4'', 4''' preferably after at least partial cooling.

Conveyor 14 effects translational movement of containers 8. Containers 8 are moved along conveyor 14 to and through the location of inspection apparatus 2. Transport means 10 engages containers 8 to assist in moving containers through inspection gauges 4. Inspection gauges 4, 4', 4'', 4''' measure various external dimensions of the containers 8 to ensure that such dimensions are within acceptable tolerances. Gauges 4, 4', 4'', 4''' also inspect containers 8 at one or more levels thereon for the presence of surface irregularities and defects. Transport means 10 also axially rotates each container 8 about a vertical axis as the container is moved through inspection gauges 4, 4', 4'', 4'''. Upon passage through gauges 4 and disengagement from transport means 10, the rotational motion of each container 8 is halted and its movement on production line 12 continues. If an inspection gauge 4, 4', 4'', 4''' detects that a container is defective, as described more fully hereinafter, the defective container may be identified and/or physically removed from production line 12 by reject means 16. Reject means 16 is in communication with inspection gauge 4, as more fully discussed hereinafter. Reject means 16 may be of any conventional variety known to those skilled in the art.

In a preferred embodiment, four inspection gauges 4 are provided. The four inspection gauges 4, 4', 4'', 4''' are relatively spaced above production line 12 and generally aligned with one another. The use of four spaced inspection gauges 4, 4', 4'', 4''' enables substantially the entire circumference of each container 8 at the levels of inspection to be inspected and also permits high production line speeds to be maintained because more than one container can be inspected simultaneously. Each inspection gauge 4, 4', 4'', 4''' inspects only one container at a time. However, the use of four inspection gauges permits up to four containers to be inspected simultaneously. The longitudinal axis of each inspection gauge 4, 4', 4'', 4''' is preferably oriented generally parallel to the direction of travel of the container along container path 6, or production line 12.

Figure 4:
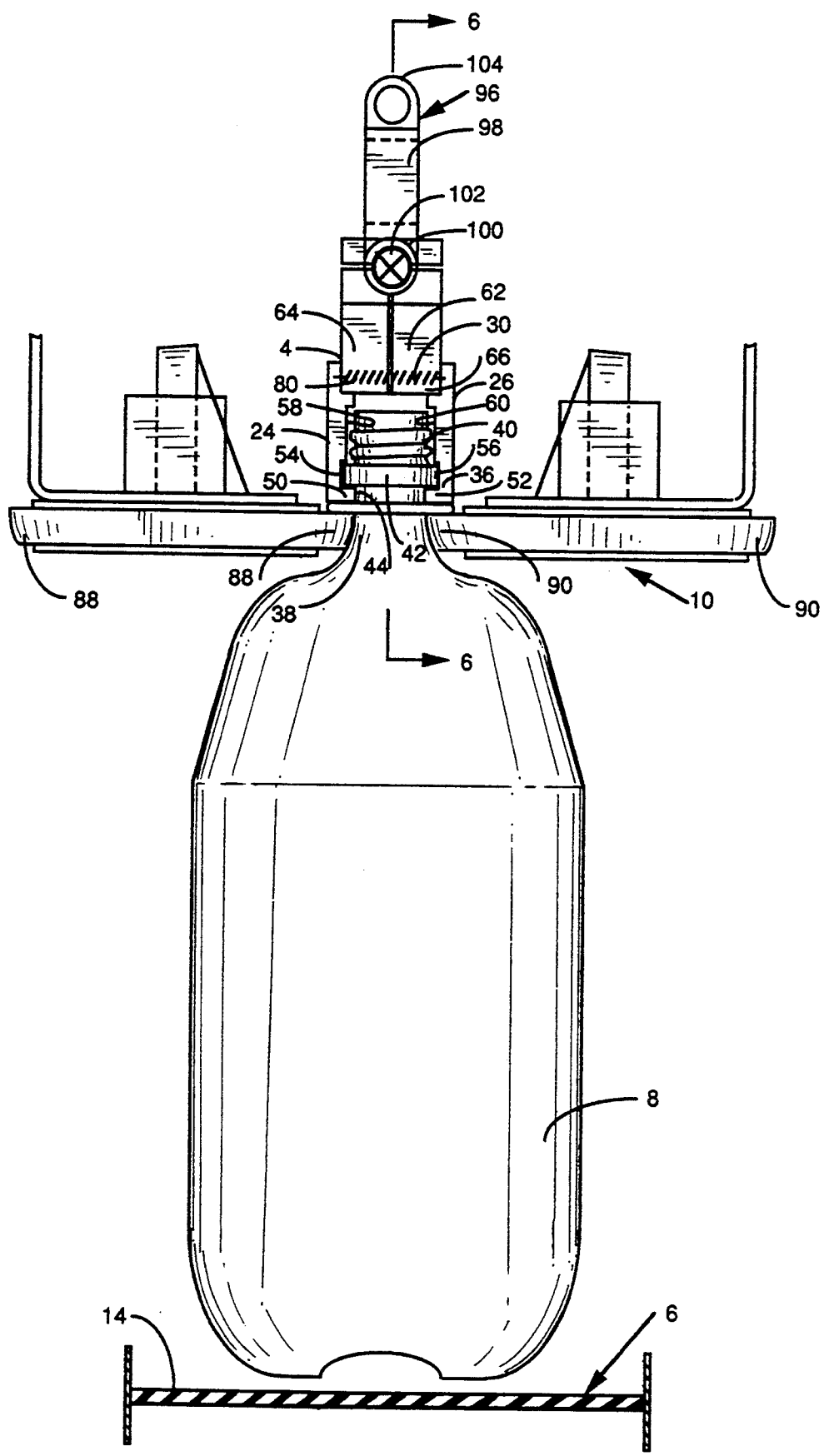
FIG. 4 is a front view of a portion of the apparatus of this invention shown in FIG. 1.
Figure 5:
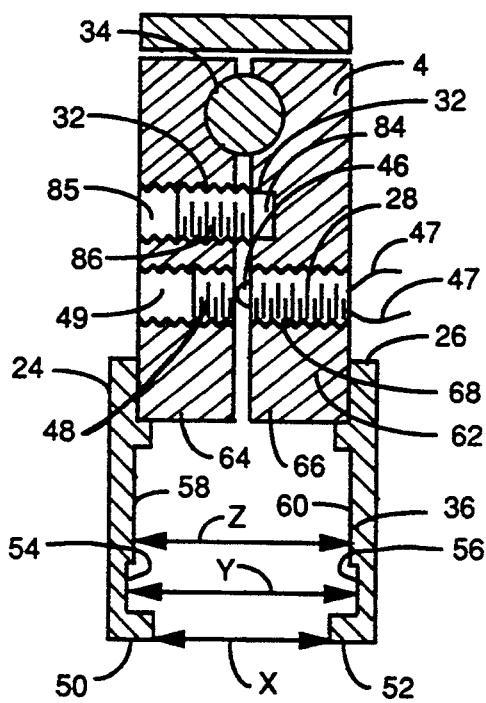
FIG. 5 is a cross-sectional view of an inspection gauge of this invention taken through line 5—5 of FIG. 3.
Figure 6:
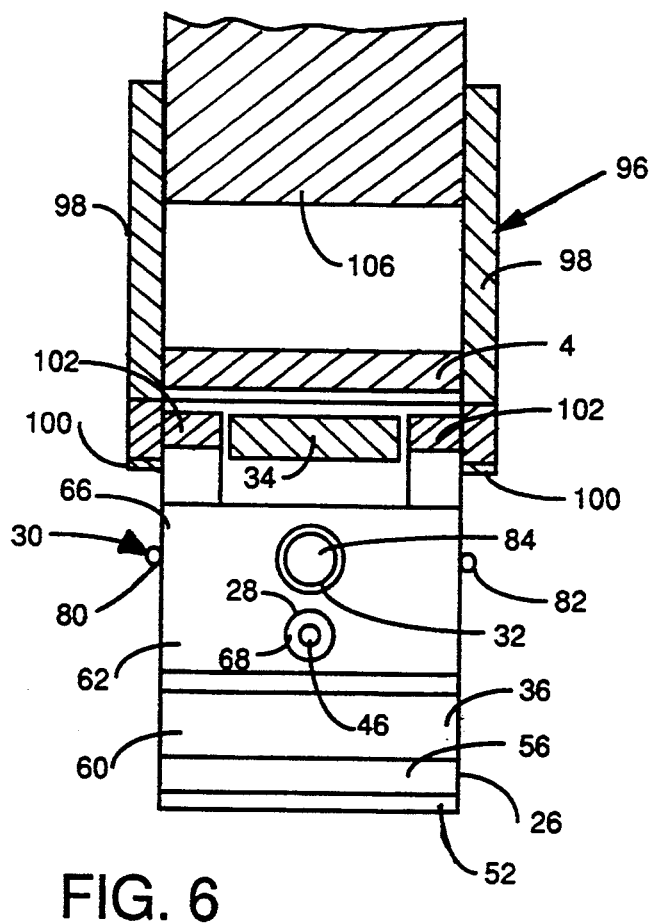
FIG. 6 is a longitudinal sectional view of the apparatus shown in FIG. 4 taken through line 6—6 of FIG. 4.

Referring now to FIGS. 4 through 6, there is shown an inspection gauge 4 of she present invention. Each inspection gauge 4 includes a pair of elongated, generally opposed gauge plates 24, 26, sensor means 28 in communication with gauge plates 24, 26 and operative responsive to movement thereof for detecting defective containers, return spring means 30 for urging gauge plates 24, 26 into the closed position, and dampening means 32 for reducing rebound movement of the gauge plates upon closure thereof.

Figure 7:
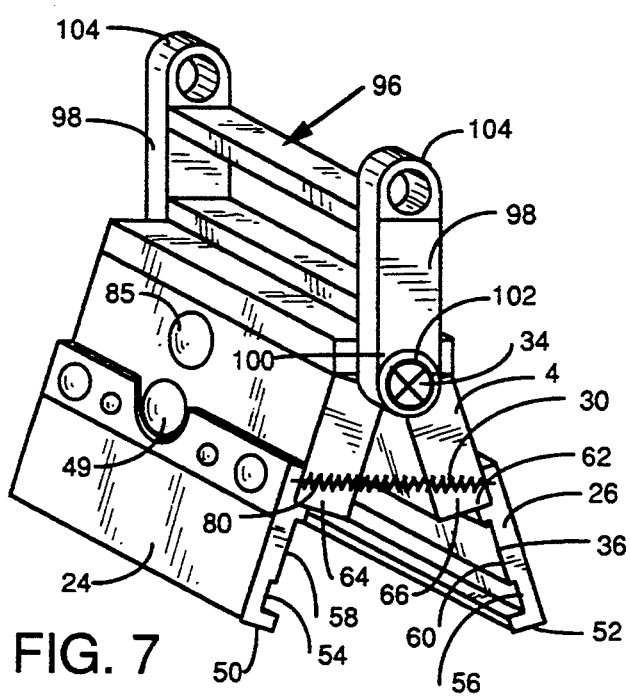
FIG. 7 is a perspective view of an inspection gauge of this invention shown in an open position.

Gauge plates 24, 26 are mounted for pivotal movement relative to one another about first pivot points 34. First pivot point 34 is preferably located on upper ends of gauge plates 24, 26. FIG. 7 shows inspection gauge 4 with gauge plates 24, 26 separated about pivot point 34. Gauge plates 24, 26 are preferably made from a high strength aluminum alloy, such as 7075-T651 alloy, which is plated with hard chrome. The aluminum alloy provides high strength and light weight and the chrome plating improves wear resistance.

Referring again to FIGS. 4 through 6, gauge plates 24, 26 have gauging means 36 thereon for engaging containers 8 passing therebetween at least one vertically spaced pair of generally diametrically opposed locations on container 8. Each such pair of locations define an inspection level. Gauging means 36 preferably extend generally longitudinally along gauge plates 24, 26 and consist of pairs of opposed raised and/or recessed regions on the interior surfaces of gauge plates 24, 26 corresponding to the desired dimensions and shapes of the containers at the areas thereof being inspected. Each pair of regions preferably has one member on plate 24 and one member on plate 26. As the container 8 is being inspected, it is rotated about its vertical axis and moved through inspection gauge 4, gauging means 36 will measure the container over its entire circumference at each location where the container is engaged by gauging means 36.

Referring still to FIG. 4 through 6, a preferred embodiment of this invention is used to inspect the exterior finish of generally cylindrical containers 8, such as blown plastic beverage bottles, for oversized exterior dimensions and exterior surface defects which cause areas of the containers to be oversized. Such beverage bottles have a neck portion 38 which includes a threaded region 40, a flanged region 42, and a skirt region 44, each of which are preferably simultaneously inspected for proper dimensions and the existence of surface defects. In a preferred embodiment, gauging means 36 includes three pairs of inspecting regions each for inspecting one of threaded region 40, flanged region 42, and skirt region 44. The first pair of inspection regions are ribs 50, 52 extending generally longitudinally along the lower portion of each gauge plate 24, 26. Ribs 50, 52 engage each container 8 at generally diametrically opposed locations on skirt region 44. Ribs 50, 52 preferably have a width, or vertical extent, of about $0.094 \pm 0.005$ inches. The distance that each rib 50, 52 projects from the generally vertical side walls of gauge plates 24, 26 will depend upon the desired dimensions of the container being inspected. In a preferred embodiment, ribs 50, 52 extend approximately $0.073 \pm 0.001$ inches from the side walls of gauge plates 24, 26.

A second pair of inspecting regions are recessed areas 54, 56 extending generally longitudinally along a portion of each gauge plate 24, 26. Recessed areas 54, 56 preferably engage each container 8 at flanged region 42, recessed areas 54, 56 preferably have a width, or vertical extent, of about $0.220 \pm 0.005$ inches. The depth of recessed areas 54, 56 will be dependent upon the desired dimensions of the containers being inspected. However, in the preferred embodiment, the depth of recessed areas 54, 56 is about $0.008 \pm 0.001$ inches.

A third pair of inspecting regions are projecting surfaces 58, 60 extending generally longitudinally along a portion of each gauge plate 24, 26. Projecting surfaces 58, 60 are preferably located above ribs 50, 52 and recessed areas 54, 56. Projecting surfaces 58, 60 preferably engage containers 8 at threaded region 40. Projecting surfaces 58, 60 preferably have sufficient width, or vertical extent, so as to contact threaded region 40 over substantially its entire vertical extent. In a preferred embodiment, the width of projecting surfaces 58, 60 is $0.500 \pm 0.005$ inches.

It will be appreciated that the transverse distance between opposed members of each pair of inspecting regions is substantially equal to the preferred diameter of the container at the location on the container where the pairs of inspecting surfaces engage the container. Accordingly, in a preferred embodiment, the distance X between ribs 50, 52 is substantially equal to the preferred by diameter of skirt region 44; the distance Y between recessed areas 54, 56 is substantially equal to the preferred diameter of flanged region 42; and the distance Z between projecting surfaces 58, 60 is substantially equal to the preferred diameter of threaded region 40. In a preferred embodiment, these dimensions will be about 0.978 inches, about 1.108 inches, and about 1.094 inches, respectively. It will be appreciated, however, that these dimensions may be varied in order to accommodate containers of any desired dimensions and configurations.

The transverse separation distance between gauge plates 24, 26 is the distance between the interior surfaces of gauge plates 24, 26. When inspection gauge 4 and gauge plates 24, 26, are in the closed position, stop means 62 maintains the desired separation distance between gauge plates 24, 26. In a preferred embodiment, stop means 62 includes spacer members 64, 66 on an upper portion of each gauge plate 24, 26 above the inspection regions. When the gauge plates 24, 26 are in the closed position, adjacent surfaces of spacer members 64, 66 abut against one another to maintain the desired separation distance. The separation distance of gauge plates 24, 26 when in the closed position is substantially equal to the desired diameter of the container at the locations to be inspected. It will be appreciated that this distance will depend upon the location on gauge plates 24, 26 where it is measured. For example, in a preferred embodiment, separation distance at ribs 50, 52 will be equal to distance X, and that separation distance will be less than the separation distance at recessed areas 54, 56, which will be equal to distance Y.

When a container 8 which has oversized dimensions in any one or more of threaded region 40, flanged region 42, and skirt region 44, or which has a finish defect in any one of those regions which creates an oversized area in that region, enters inspection gauge 4, the oversized area will force apart the pair of inspection regions engaging the oversized area of the container so that the container can pass through inspection gauge 4. The separation of the pairs of inspection regions is accomplished by pivotal relative movement of gauge plates 24, 26 about first pivot points 34. When a defective container passes through inspection gauge 4, the relative separation distance between gauge plates 24, 26 increases.

Sensor means 28 is operative responsive to relative movement of gauge plates 24, 26 for detecting defective containers. Sensor means 28 detects defective containers when the relative separation distance between gauge plates 24, 26 at the locations where gauge plates 24, 26 contact container 8 falls outside predetermined limits. As discussed hereinbefore, in a preferred embodiment, defective containers are those which have oversized dimensions at any of the inspected locations or which have finish surface defects in any of those locations which causes the diameter in the area of the surface defect to exceed the desired diameter. Accordingly, a defective container is detected when the separation distance between gauge plates 24, 26 exceeds a predetermined amount.

Referring to FIG. 5, in a preferred embodiment, each sensor means 28 includes a microswitch 68 which is open when gauge plates 24, 26 are in the closed position. Microswitch 68 is preferably mounted on one of spacer members 64, 66. In a preferred embodiment, microswitch 68 is mounted on spacer member 66. A spring loaded switch activator 46 projects generally inwardly toward the opposite spacer member 64. Switch trip-point adjustor 48 is mounted on spacer member 64 directly opposite switch activator 46. When inspection gauge 4 is closed, switch trip-point adjustor 48 contacts switch activator 46, forcing switch activator 46 inwardly, thereby opening microswitch 68. Switch trip-point adjustor 48 is preferably provided with threads which cooperate with threads on an opening 49 in spacer member 64 into which it is mounted. The lateral position of switch trip-point adjustor 48 may be adjusted by screwing it into or out of opening 49. Adjusting the position of switch trip-point adjustor 48 allows the predetermined limit of the separation distance of gauge plates 24, 26 at which microswitch 68 is activated to be adjusted, thereby enabling the inspection gauge 4 to be used to inspect various size containers. The threads for adjusting the lateral position of switch trip-point adjustor 48 are preferably extremely fine such that the lateral position of adjustor 48 may be adjusted to within very small tolerances. This allows inspection gauge 4 to be calibrated to detect very small defects on or variation in the dimensions of the containers being inspected.

Figure 8:
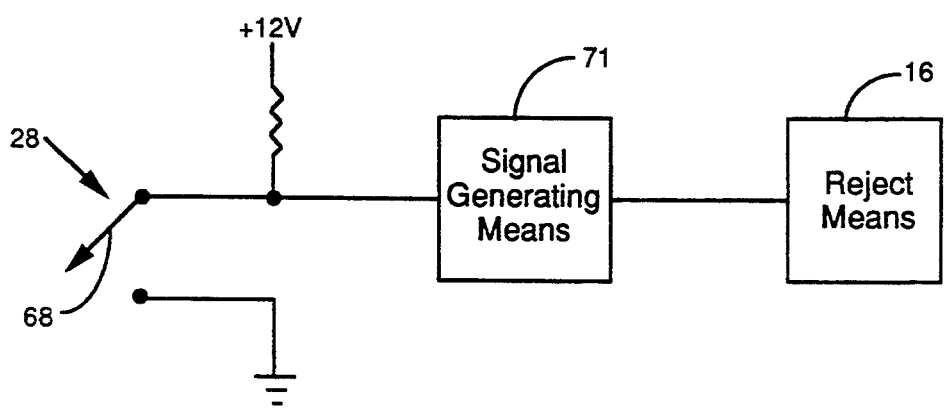
FIG. 8 is a schematic diagram of the operation of one embodiment of the sensor means and reject means of this invention.

Referring now to FIGS. 5 and 8, when the separation distance between gauge plates 24, 26 caused by a defective container passing therebetween exceeds a predetermined limit, microswitch 68 closes, thereby causing an electrical signal to be generated by signal generator means 71 and transmitted to reject means 16. Microswitch 68 is electrically connected to signal generator means 71 by leads 47. The transmission of the electrical signal to reject means 16 identifies the defective container. In a preferred embodiment, reject means 16 includes a rejection assembly 69 (FIG. 1) for physically removing the identified defective container from production line 12. In a preferred embodiment, reject means 16 is an electromechanical device in which rejection assembly 69 physically removes the defective containers from the production line using a blast of air directed at the defective containers. This type of rejection means is known to those skilled the art. In addition, it will be appreciated that any other suitable type of reject means known to those skilled in the art may be utilized.

In order to ensure that only the containers that have been identified as defective are rejected, or removed from the production line, a tracking system is used to track the container moving through the inspection gauges. The tracking system uses an encoder which runs on conveyor 14 and which is electrically connected to reject means 16. Such tracking systems are known to those skilled in the art.

The use of microswitch 68 allows inspection gauge 4 to very accurately detect defective containers. In addition, the system may be calibrated such that very small variations in the separation distance between the gauge plates will cause microswitch 68 to open, thereby detecting containers which have very small defects, but which nonetheless render the containers defective.

Figure 9:
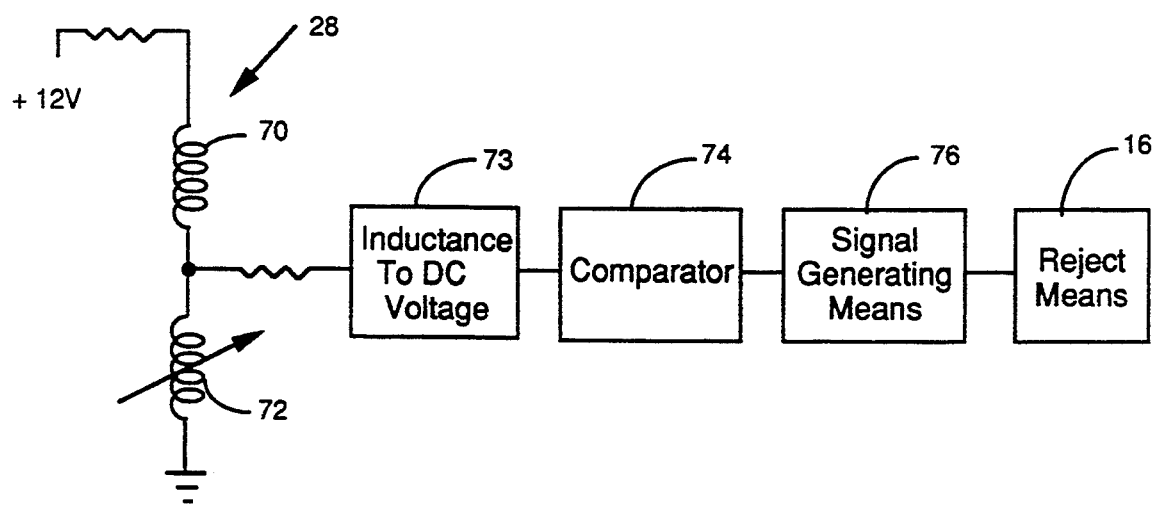
FIG. 9 is a schematic diagram of the operation of another embodiment of the sensor means and reject means of this invention.

Referring now to FIG. 9, there is shown another embodiment of sensor means 28. In this embodiment, sensor means 28 include a pair of ferrite coils 70, 72. Coils 70, 72 are connected to gauge plates of the inspection gauge and are relatively positioned such that they produce a predetermined inductance when the gauge plates are in the closed position. When a defective container passes through the inspection gauge, the separation distance between the gauge plates increases, thereby causing the distance between the coils 70, 72 to increase. The change in the relative positions of coils 70, 72 causes the inductance to decrease. The inductance is changed to a DC voltage at converter 73 and transmitted to comparator 74, where it is compared to a predetermined voltage. If the DC voltage received from coils 70, 72 is the same as the reference voltage, the container is considered acceptable. If the DC voltage received from coils 70, 72 is different from the reference voltage, then an electrical signal is generated by signal generating means 76 and transmitted to reject means 16, which identifies the defective container and removes it from the production line as discussed hereinbefore. This type of sensor can also be calibrated for very high accuracy and to detect very small defects.

Because the embodiments of sensor 28 shown in FIGS. 8 and 9 can both be calibrated to detect very small defects on the containers, it is important that pivot point 34 have little or no play therein. If there is play in first pivot point 34, it may result in rejection of acceptable containers, acceptance of defective containers and/or complete malfunction.

Referring again to FIGS. 4-7, as described hereinbefore, when defective containers pass through inspection gauges 4, gauge plates 24, 26 pivotally separate about pivot point 34. When the defective container exits the gauges 4, return spring means 30 urges gauge plates 24, 26 into the closed position. In a preferred embodiment, return spring means 30 includes two springs 80, 82, one of which is mounted on each end of gauge 4. Springs 80, 82 preferably provide relatively high restoring force to urge gauge plates 24, 26 closed.

Dampening means 32 also assists in urging gauge plates 24, 26 closed and holding gauge plates 24, 26 closed as non-defective contains pass through inspection gauge 4. Another major function of dampening means 32 is to hold gauge plates 24, 26 in the closed position and to reduce rebound movement of gauge plates 24, 26 upon closure thereof. If gauge plates 24, 26 rebound when they are closed after the exit of a defective container, the next container in the sequence could be prematurely, or incorrectly, identified as defective by sensor means 28 and rejected. Dampening means 32 reduces the likelihood of rebound movement occurring, thereby reducing the likelihood that false detection of defective containers will occur.

In a preferred embodiment, dampening means 32 is a magnetic damper which includes a permanent magnet 84 and a generally opposed adjustable magnetic stop screw 86 which are mounted on the abutting sides of spacer members 64, 66. In a preferred embodiment, magnet 84 is mounted on spacer member 66 and stop screw 86 is mounted on spacer member 64. As gauge plates 24, 26 close, magnet 84 attracts stop screw 86 and thereby holds gauge plates 24, 26 closed and prevent rebound movement thereof.

Adjustable stop screw 86 may be provided with threads which cooperate with threads on opening 87 in stop member 64 into which stop screw 86 is mounted to adjust the lateral position of stop screw 86. Adjusting the lateral position of stop screw 86 enables the separation distance between gauge plates 24, 26 to be adjusted to accommodate containers of various sizes. It will be appreciated that in order to adjust inspector gauge 4 to accommodate different sized containers, it may be necessary to adjust both stop screw 86 and switch trip-point adjustor 48 to ensure that all defective containers and only defective containers are rejected.

Referring to FIGS. 1 through 4 there is shown transport means 10 which is provided to move or assist in moving containers 8 through inspection gauges 4 for inspection while axially rotating the containers about a vertical axis. Transport means 10 may also lift containers 8 slightly off of conveyor 14, in which case transport means 10 alone moves the containers 8 through inspector gauge 4. In order to lift containers 8 off of conveyor 14, transport means 10 is preferably slightly inclined with the end where containers 8 enter transport means 10 being slightly lower than the end where containers 8 exit from transport means 10. In a preferred embodiment, transport means 10 includes a pair of endless drive belts 88, 90 disposed generally longitudinally adjacent to inspection gauges 4, 4', 4'', 4'''. Belts 88, 90 are preferably positioned below inspection gauges 4 and on opposite sides of container path 6, such that belts 88, 90 will engage containers 8 on generally opposite sides thereof below neck 38 of containers 8. Belts 88, 90 preferably engage containers 8 shortly before the containers enter upstream end 92 of inspection gauges 4. The distance between belts 88, 90 is governed by the diameter of the area of the containers 8 which the belts engage. In a preferred embodiment, the distance between belts 88, 90 is about 1.063 inches for containers having a 28 mm finish. The outer surfaces of drive belts 88, 90 which engage containers 8 may preferably be formed so as to correspond to the shape of the exterior of the area of the containers 8 which belts 88, 90 engage. This enables the entire surfaces of the belts 88, 90 to contact the container, thereby improving the frictional engagement between belts 88, 90 and containers 8.

In order to axially rotate containers 8 while simultaneously moving them forward, one of the drive belts 88, 90 travels slightly faster than the other drive belt. The speed differential between the belts is such that each container 8 makes at least one-half of one revolution as it passes through the total length of inspection gauges 4. This, combined with the total length of gauge plates 24, 26, enables each container to be inspected about substantially its entire circumference where it is engaged by gauge plates 24, 26. Rotation of defective containers also assists in such containers opening, or separating, gauge plates 24, 26. The rotating defective containers may cam open gauge plates 24, 26.

Drive belts 88, 90 extend past downstream end 94 of inspection gauges 4. Once a container 8 has traveled the length of drive belts 88, 90, the container is disengaged from belts 88, 90 and deposited back onto conveyor 14, where the rotational movement of the container is stopped.

In a preferred embodiment, rotational movement of the containers is stopped by stabilizer wheel 91. Stabilizer wheel 91 includes a soft tire 93 which engages an upper portion of containers 8 as they are disengaged from drive belts 88, 90. Tire 93 forces the containers 8 down onto conveyor 14 and stops the rotational movement of the containers 8. Stabilizer wheel 91 preferably is rotated in the direction indicated by arrow W such that the portion of tire 93 which engages containers 8 is moving at substantially the same speed and in substantially the same direction as conveyor 14. Wheel 91 may be rotated using a conventional drive system of a type known to those skilled in the art.

Drive belts 88, 90 also control the spacing of the containers as they pass through inspection gauges 4 to ensure that only one container at a time is located within any inspection gauge. After the containers emerge from between drive belts 88, 90, rejection assembly 69 physically removes from the production line 12 defective containers identified by gauges 4.

It will be appreciated that this invention may be used to inspect each container 8 moving on conveyor 14. However, it may be desirable to discontinue container inspection without disrupting the flow of containers. In addition, it may be desirable to restart inspection without disrupting container flow. In order to accomplish intermittent starting and stopping of container inspection without disrupting container flow, means may be provided for sequentially opening gauges 4, 4', 4'', 4''', such that containers 8 are not being inspected, and retracting transport means 8, such that containers 8 are not engaged by drive belts 88, 90. This permits containers 8 to be moved through the inspection area of the production line without encountering the inspection apparatus 2. To restart inspection, means are provided for sequentially moving transport means 10 back into a position to engage containers 8, and then closing inspection gauges 4, 4', 4'', 4''' such that containers 8 are passing before gauge plates 24, 26 for inspection. It will be appreciated that such movements of transport means 10 and inspection gauges 4, 4', 4'', 4''' may be accomplished without disrupting the flow of containers 8 on conveyor 14. Any suitable means may be utilized to open and close inspection gauges 4, 4', 4'', 4'''. For example, an electric motor connected to gears in communication with the inspection gauges to open and close the gauges may be used. Likewise, any suitable means may be utilized to move transport means 10 into and out of the inspection position. For example, electric motors using gear or pulley drives to move transport means 10 into and out of the inspection position may be provided. In addition, conventional control circuitry may be utilized to control the sequence of inspection gauge opening and closing and transport means movement.

The length of belts 88, 90 is governed by the total length of gauge plates 24, 26 in all of the inspection gauges 4, 4', 4'', 4''' of the device. Drive belts 88, 90 are preferably longer than the total length of gauge plates 24 or 26 of all of the inspection gauges 4, 4', 4'', 4'''. This enables the containers 8 to be fully engaged by belts 88, 90 before entering the upstream end 92 of the device and to have exited and be some distance from downstream end 94 of the device before being disengaged by belts 88, 90.

The length of the gauge plates 24, 26 is determined by the circumference of the containers 8 at the levels where they are being inspected. In a preferred embodiment, the total length of the gauge plates 24 or 26 in all four inspection gauges 4, 4', 4'', 4''' is substantially equal to about two or four times the circumference of containers 8 in neck area 38. That length ensures that the entire circumference of the containers is measured at regions 40, 42, 44 and enables the rotational speed which must be imparted to containers 8 by drive belts 88, 90 to be minimized. Minimizing the rotational speed of containers 8 is important because the types of containers which are inspected using this device are typically unstable while moving on a conveyor. The use of four inspection gauges in series enables more than one container 8 to be simultaneously inspected by the apparatus and also assist in minimizing the rotational speed which must be imparted to containers 8.

Four inspection gauges 4, 4', 4'', 4''' are provided in a preferred embodiment, as shown in FIGS. 1–3. However, it will be appreciated that more or fewer inspection gauges may be used. The number of inspection gauges may be determined by the diameter of the containers being inspected to ensure that the entire circumference of each container is inspected at the desired level and by the speed at which the apparatus is to operate.

Each gauge plate 24, 26 of each inspection gauge 4, 4', 4'', 4''' is preferably shorter in length than the smallest diameter of the containers 8 at the levels where they are being inspected. In a preferred embodiment, the length of each gauge plate 24, 26 is about 50 to 65 percent of the circumference of the container at the level being inspected which has the smallest diameter. This length ensures that only one container at a time can be in each inspection gauge 4, 4', 4'', 4'''.

The distance between each of the spaced inspection gauges 4 is preferably about ½ to ¾ inches. The distance between the gauges is governed by the amount of space needed for the suspension system which is discussed more fully hereinafter. However, this dimension may be varied depending upon container size. It has been found that these dimensions and spacings enable generally cylindrical, blown plastic containers, such as "two-liter" soft drink containers having dimensions as discussed hereinbefore, to be inspected at production line speeds of up to 25,000+ containers per hour.

Ideally, each container is concentric about its longitudinal, or vertical, axis. However, occasionally, some of the containers being inspected are non-concentric. One example of a non-concentric container is where the mouth of the container and base of the container are axially displaced with respect to one another. Another example of a non-concentric container is where the mouth of the container and the base of the container are not parallel to one another and are not perpendicular to the vertical axis of the container. Such non-concentric containers may still be usable if other dimensions of the container are within acceptable tolerances. Accordingly, it may be necessary to inspect such containers for defects without the container being identified as defective because of its being non-concentric. When such a container is rotated about its vertical axis, the eccentricity of the container may cause transverse movement of the portions of the container which are being inspected. If inspection gauges 4 are fixed in position, such transverse movement may separate gauge plates 24, 26, resulting in the non-concentric container being identified as defective, even though its other dimensions may be acceptable.

Referring to FIGS. 1, 2, 4 and 6, there is shown a suspension system 96 for suspending gauges 4, 4', 4'', 4''' above container path 6 so as to permit transverse movement of each gauge when non-concentric containers pass therethrough. Suspension system 96 preferably includes at least one suspension bar 98 having one end 100 thereof pivotally connected to inspection gauge 4 at a second pivot point 102. Second pivot point 102 preferably is located at or above first pivot point 34 and on an upper portion of inspection gauge 4 above engagement means 36. The other end 104 of suspension bar 98 is preferably pivotally connected to a frame 106. Frame 106 is used in a preferred embodiment to support gauges 4 and transport means 10. It will be appreciated that the two pivotal connections of suspension bar 98 permit transverse movement of gauges 4 while allowing the gauge plates 24, 26 to be oriented so as to accept non-concentric containers therebetween. In a preferred embodiment, two suspension bars 96 are provided on each inspection gauge 4, one suspension bar 96 is positioned at each end of each inspection gauge 4.

The method of this invention includes providing a container apparatus as described hereinbefore, moving containers to be inspected through the apparatus such that the gauge plates of the inspection gauge of the apparatus engage the container at at least one pair of generally diametrically opposed locations to inspect the finish of the container at each of those locations. Further, the method includes rotating the container about its vertical axis as it passes through the inspection gauges of the apparatus such that the container is inspected over its entire circumference where engaged by the gauge plates. The method also includes pivoting each inspection gauge about at least one second pivot point to allow non-concentric containers to pass therethrough. In a preferred embodiment of the method, the containers being inspected have a neck region and at least one circumferential portion of the neck portion is inspected. In addition, the neck portion of the container preferably has external threads thereon and those threads an preferably inspected.

In a preferred embodiment of this invention, more than one container may be inspected simultaneously by moving the containers through the inspection gauges such that only one container is within each inspection gauge at a time.

The method of this invention also may include generating an electrical signal to activate reject means when a defective container is detected.

While the preferred embodiment of this invention, as described hereinbefore, may be used to inspect containers for oversized exterior dimensions and surface irregularities or defects which make the dimensions of the container at the locations of such defect oversized, it will be appreciated that this device could also be used to inspect and detect undersized dimensions and defects, and undersized and oversized defects simultaneously. In addition, while the preferred embodiment of this invention is used to inspect blown plastic bottles, it will be appreciated that any type of container made of any type of glass, plastic, or other suitable material may be inspected using this invention. It will also be appreciated that containers of any size may be inspected using this invention by varying the size and spacing of the gauge plates and/or the size, spacing and number of inspection gauges provided.

It will be appreciated that this invention provides an apparatus and method for inspecting the finish of containers which provide simple and reliable measurement of the finished dimensions of and detection of finished defects on containers at more than one level on such container simultaneously while the containers are moving at relatively high speed in a predetermined path.

Whereas particular embodiments of the invention have been described hereinbefore for purposes of illustration, it will be evident to this skilled in the art that numerous variations in the details may be made without departing from the invention as defined in the appended claims.

What is claimed is:

1. A method of inspecting exterior finish of containers moving sequentially in a predetermined path, comprising the steps of:
   providing an apparatus for inspecting exterior finish of containers, said apparatus having at least one inspection gauge having a pair of elongated, opposed gauge plates mounted for pivotal movement relative to one another about first pivot points on upper ends thereof, said gauge plates having gauging means thereon for engaging said container at at least one pair of generally diametrically opposed locations thereon, each said pair of locations being at a level on said container different from other said pairs of locations, sensor means operative responsive to relative pivotal movement of said gauge plates for detecting defective containers, said sensor means detecting defective containers when relative separation distance of said gauge plates where said gauge plates engage said containers caused by said container passing therebetween falls outside of predetermined limits, return spring means for urging said gauge plates in a closed position, and dampening means for reducing rebound movement of said gauge plates upon closure thereof;
   moving said containers sequentially and generally continuously through said apparatus;
   rotating said container about its vertical axis as it passes through said inspection gauge, whereby said gauge plates contact said container over at least its entire circumference at each said pair of locations engaged by said gauge plates;
   pivoting said inspection gauge about at least one second pivot point located at or above said first pivot point to allow non-concentric containers to pass therethrough; and
   stopping said rotation of said container after it passes through said gauge plates.

2. The method of claim 1, further including:
   moving said containers sequentially through said apparatus so that only one container at a time is within each inspection gauge such that more than one container is simultaneously inspected at more than one level on each said container.

3. The method of claim 2, further including:
   simultaneously inspecting a circumferential portion of said container at more than one vertically spaced level thereon.

4. The method of claim 3, further including:
   inspecting at least one vertically spaced circumferential portion of a neck region of said container, said neck region having external threads on a portion thereof.

5. The method of claim 4, further including:
   inspecting a circumferential portion of said external threads.

6. The method of claim 5, further including:
   generating an electrical signal to activate reject means when said sensor means detects a defective container.

7. Apparatus for inspecting exterior finish of containers moving in a predetermined path, said apparatus comprising:
   at least one inspection gauge disposed above the path, each said inspection gauge having a pair of elongated, opposed gauge plates mounted for pivotal movement relative to one another at first pivot points on upper ends thereof, said gauge plates having gauging means thereon for engaging containers passing therebetween at at least one pair of generally diametrically opposed locations on said container, with each said pair of locations being disposed at a level on said containers separate from other said pairs of locations, sensor means operative responsive to relative pivotal movement of said gauge plates for detecting defective containers, said sensor means detecting a defective container when relative separation distance between said gauge plates where said gauge plates contact said container caused by said container passing therebetween falls outside predetermined limits, return spring means for urging said gauge plates into a closed position, stop means for maintaining a predetermined relative separation distance between said gauge plates when in said closed position, and dampening means for reducing rebound movement of said gauge plates upon closure thereof, said dampening means includes a magnetic damper on said stop means;

said gauge plates having a total length along the path such that each container passing therebetween is inspected about its entire circumference at each level where said container is engaged by said gauge plates;

said sensor means having at least one adjustable microswitch on said stop means which is activated when separation distance of said gauge plates falls outside said predetermined limits;

transport means for moving said containers sequentially through each said gauge and axially rotating each said container about its vertical axis, said transport means including a pair of endless drive belts disposed generally longitudinally adjacent to said inspection gauges and positioned to engage opposite sides of said containers travelling through said inspection gauges, one said drive belt travelling faster than another said drive belt, whereby each container engaged by said drive belts will be propelled longitudinally along said drive belts and simultaneously be rotated about its vertical axis, said transport means further includes a container stabilizer wheel having a soft tire thereon rotatably mounted so as to engage said containers upon disengagement from said drive belts, whereby rotational movement of said containers is stopped; and each said inspection gauge being suspended above the path by a suspension system which permits each said gauge plate to pivot in a transverse direction about at least one second pivot point at or above said first pivot point to receive non-concentric containers therethrough, said suspension system includes at least one suspension bar having one end thereof pivotally connected to an inspection gauge and having another end thereof pivotally connected to a frame for supporting said gauges, whereby transverse pivotal movement of said gauges may be achieved.

8. The apparatus of claim 7, further comprising
means for selectively opening and closing each said inspection gauges; and
means for selectively moving said transport means into and out of position, whereby container inspection may be selectively stopped and started without disrupting said moving containers.

9. The apparatus of claim 7, wherein
each said containers has a neck region having external threads on a portion thereof; and
said gauge plates have means thereon for engaging said neck region at least one vertically spaced pair of generally diametrically opposed locations.

10. The apparatus of claim 9, further comprising
reject means in communication with said sensor means for identifying defective containers detected by said sensor means.

11. The apparatus of claim 10, wherein
said reject means includes a rejection assembly for physically removing defective containers from the path.

12. The apparatus of claim 11, wherein
said reject means further includes signal generating means electrically connected to said rejection assembly and in communication with said sensor means for generating an electrical signal which activates said rejection assembly when a defective container is detected.

13. The apparatus of claim 12, wherein
activation of said microswitch activates said reject means.

14. The apparatus of claim 9, wherein
said gauge plates have gauging means thereon for engaging each said container passing therebetween at more than one vertically spaced pair of generally diametrically opposed locations, whereby the diameter of said container can be measured and surface irregularities on said container may be inspected for about substantially the entire circumference of said container at each level of each said pair of locations.

15. The apparatus of claim 14, wherein
at least one said pair of vertically spaced locations is on said external threads.

16. The apparatus of claim 13, wherein
four said inspection gauges relatively spaced longitudinally along said path are provided with the total length of said gauge plates of all said inspection gauges being substantially equal to about 2 to 4 times the circumference of each said container at the levels being inspected and the length of each said gauge plate of each said inspection gauge is shorter than the smallest diameter of said container at the level being inspected, whereby more than one container can be simultaneously inspected about their entire circumferences-at the levels of each said pair of locations.

17. The apparatus of claim 16, wherein
said gauges are spaced apart along the path by a distance sufficient to accommodate said suspension system.

18. The apparatus of claim 17, wherein
said path extends generally longitudinally along a production line.

* * * * *